(12) United States Patent
Patek

(10) Patent No.: US 11,179,095 B2
(45) Date of Patent: Nov. 23, 2021

(54) METHOD, SYSTEM, AND APPARATUS FOR REMOTE PATIENT MONITORING OR TRACKING OF SEPSIS-RELATED INDICATORS

(71) Applicant: UNIVERSITY OF VIRGINIA PATENT FOUNDATION, Charlottesville, VA (US)

(72) Inventor: Stephen D. Patek, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 71 days.

(21) Appl. No.: 16/097,526

(22) PCT Filed: Apr. 28, 2017

(86) PCT No.: PCT/US2017/030052
§ 371 (c)(1),
(2) Date: Oct. 29, 2018

(87) PCT Pub. No.: WO2017/189957
PCT Pub. Date: Nov. 2, 2017

(65) Prior Publication Data
US 2019/0125241 A1 May 2, 2019

Related U.S. Application Data

(60) Provisional application No. 62/329,447, filed on Apr. 29, 2016.

(51) Int. Cl.
| | | |
|---|---|---|
| A61B 5/00 | (2006.01) | |
| A61B 5/0205 | (2006.01) | |
| A61B 5/024 | (2006.01) | |
| A61B 5/11 | (2006.01) | |
| G16H 40/67 | (2018.01) | |
| A61B 5/08 | (2006.01) | |
| G16H 50/30 | (2018.01) | |
| A61B 5/021 | (2006.01) | |

(52) U.S. Cl.
CPC ............ *A61B 5/412* (2013.01); *A61B 5/0022* (2013.01); *A61B 5/024* (2013.01); *A61B 5/02055* (2013.01); *A61B 5/08* (2013.01); *A61B 5/1118* (2013.01); *A61B 5/7203* (2013.01); *A61B 5/7221* (2013.01); *A61B 5/7275* (2013.01); *G16H 40/67* (2018.01); *G16H 50/30* (2018.01); *A61B 5/021* (2013.01); *A61B 5/0816* (2013.01); *A61B 2505/07* (2013.01); *A61B 2562/0219* (2013.01)

(58) Field of Classification Search
USPC ................................................ 600/300, 301
See application file for complete search history.

(56) References Cited

U.S. PATENT DOCUMENTS

| | | | | |
|---|---|---|---|---|
| 2009/0149724 A1* | 6/2009 | Mark | ....................... | A61B 5/00 600/300 |
| 2012/0123232 A1* | 5/2012 | Najarian | ................ | G16H 40/67 600/345 |
| 2012/0245439 A1* | 9/2012 | Andre | .................... | A61B 5/412 600/310 |

* cited by examiner

*Primary Examiner* — Nicole F Lavert
(74) *Attorney, Agent, or Firm* — Potomac Law Group, PLLC; Vincent M DeLuca

(57) ABSTRACT

A method, system, and apparatus for remote patient monitoring or tracking sepsis-related indicators or markers in ambulatory patients or outpatients. The method, system, and apparatus is devised or configured to provide remote patient monitoring of patient vitals signs for determining the risk for sepsis.

15 Claims, 8 Drawing Sheets

HEART RATE (MONITOR CONTINUOUSLY)
- IF AVERAGE* IS < 1/2 (220 - AGE) bpm, FLAG IS 0.
- IF AVERAGE IS > 1/2 (220 - AGE) bpm AND
  - ACTIVITY IS 1, FLAG IS 0.
  - ACTIVITY IS 0, FLAG IS 1.

*AVERAGE HEART RATE OVER THE LAST 15 MINUTES (NO FLAG THROWN IN FIRST 15 MINUTES)

RESPIRATORY RATE (MONITOR CONTINUOUSLY)
- IF AVERAGE* IS BETWEEN 8-19 bpm, FLAG IS 0.
- IF AVERAGE IS < 8 bpm, FLAG IS 1.
- IF AVERAGE IS > 20 bpm AND
  - ACTIVITY IS 1, FLAG IS 0.
  - ACTIVITY IS 0, FLAG IS 1.

*AVERAGE BREATHING RATE OVER THE LAST 15 MINUTES (NO FLAG THROWN IN FIRST 15 MINUTES)

TEMPERATURE & BLOOD PRESSURE (TWO MONITORING SCHEDULES)

NORMAL*: 9AM, 3PM, 9PM
- IF BETWEEN 96.8F - 100.4F, FLAG IS 0.
- IF BELOW 96.8F OR GREATER THAN 100.4F, FLAG IS 1, SHIFT TO HIGH FREQUENCY PROBING SCHEDULE.

HIGH FREQUENCY*: 9AM, 12PM, 3PM, 6PM, 9PM
- IF BETWEEN 96.8F - 100.4F, FLAG IS 0.
- IF BELOW 96.8F OR GREATER THAN 100.4F, FLAG IS 1.
- IF 6 FLAGS ARE 0 IN A ROW, SHIFT TO NORMAL SCHEDULE.

*IF ACTIVITY WITHIN LAST 30 MINUTES, DELAY PROMPT BY 30 MINUTES

SUSPECTED INFECTION (PROBE AT END OF DAY)
- PROMPT: DID YOU EXPERIENCE ANY OF THESE SYMPTOMS IN THE LAST 24 HOURS?  *CHECKLIST INCLUDES CHILLS, DIARRHEA, VOMITING, ETC.
  - IF 2+ SYMPTOMS ARE CHECKED IN THE CHECKLIST*, THEN FLAG IS 1.

ACTIVITY (MONITOR CONTINUOUSLY)
- IF ACCELEROMETER VALUES PEAK 2 STDEV FROM AVERAGE NOISE LEVEL OR HR IS >50% OF MAXIMUM AND
  - VITALS PEAK 10-60 SECONDS OR MORE THAN 5 MINUTES, PROMPT PATIENT TO CONFIRM IF HE IS EXERCISING, FLAG IS 0.
  - VITALS ABOVE 50% OF MAX FROM 1 - 5 MINUTES, PROMPT PATIENT TO CONFIRM IF HE IS EXERCISING, FLAG IS 1.
- IF ACCELEROMETER VALUES < 2 STDEV FROM AVERAGE NOISE LEVEL OR HR IS <50% OF MAXIMUM, FLAG IS 0.

FIG. 1

TABLE I

FINDINGS OF OUR RESEARCH

| DESIGN CONSIDERATION | FINDING |
|---|---|
| PATIENT ACTIVITY | ACTIVITY CAN CONFOUND DATA, FALSE INDICATOR |
| BASELINING VITALS | ENABLE BASELINING OF INDIVIDUAL VITAL SIGNS AUTOMATICALLY OR MANUALLY |
| PATIENT INVOLVEMENT | CONSIDER USER WHEN DESIGNING TO ENSURE MAXIMAL COMPLIANCE |
| QUALITY OF DEVICES | SENSORS SHOULD BE ACCURATE, OPEN-SOURCE, FDA-APPROVED |
| COMMUNICATION OF FINDINGS | DAILY REPORTS ARE MORE EFFECTIVE THAN NOTIFICATIONS |

*FIG. 5*

PROTYPE DESIGN

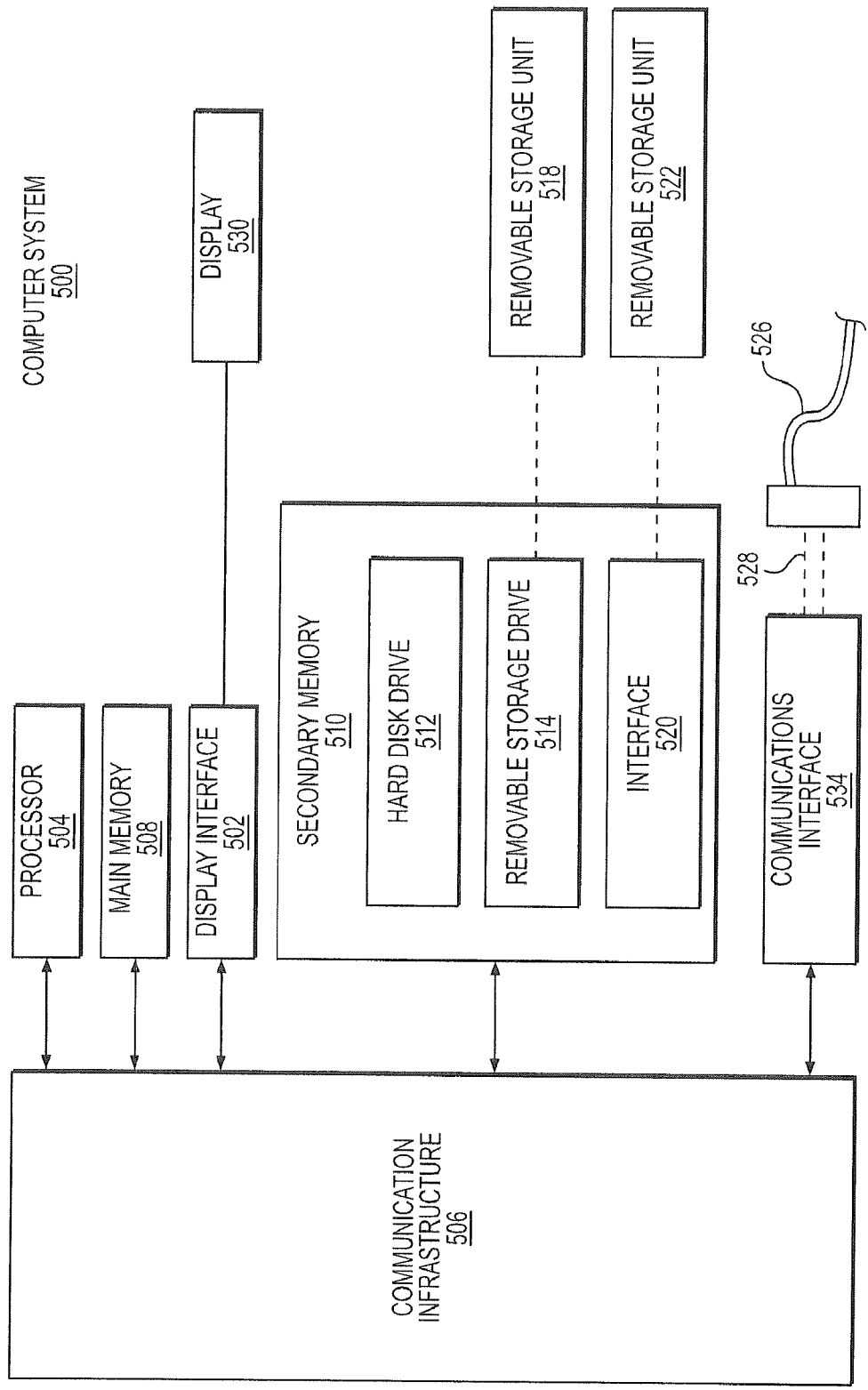

METHOD, SYSTEM, AND APPARATUS FOR REMOTE PATIENT MONITORING OR TRACKING OF SEPSIS-RELATED INDICATORS

RELATED APPLICATION

This is a U.S. non-provisional patent application of U.S. provisional patent application No. 62/329,447, filed on Apr. 29, 2016, which is incorporated herein by reference. This U.S. non-provisional patent application claims priority to this U.S. provisional patent application No. 62/329,447 under 35 U.S.C. § 119(e).

FIELD

The present invention relates to a method, system, and apparatus for remote monitoring or tracking of sepsis-related indicators or markers in ambulatory patients or outpatients. For example, a method, system, and apparatus for remote patient monitoring for improving outpatient care of patients as risk for sepsis.

BACKGROUND

As a leading cause of death in the Intensive Care Unit (ICU) and one of the main contributors to hospital readmission rates, sepsis poses a significant healthcare problem in the United States. The traditional understanding of sepsis focused on infection, but new guidelines have changed the focus to a, "life-threatening organ dysfunction caused by a dysregulated host response to infection" (see Jacob, J. A. (2016). New sepsis diagnostic guidelines shift focus to organ dysfunction. JAMA, 315(8), 739-740. doi:10.1001/jama.2016.0736).

Sepsis treatment in the hospital currently reacts to the disease, but there are not many proactive measures outside of the hospital setting that effectively monitor for sepsis risk indicators. However, studies suggest that early detection of risk indicators can reduce its toll on mortality and readmission rates. Post-operative outpatients recently discharged from the hospital have a high risk of developing sepsis, making them viable candidates to attempt early detection. This study considers problems associated with outpatient sepsis monitoring and proposes a remote monitoring solution that incorporates a commercial off-the-shelf wireless biometric device to monitor changes in patient vitals and provide early warning signs of sepsis. In 2010, the Patient Protection and Affordable Care Act (known as ACA) established a national Hospital Readmissions Reduction Program (HRRP), holding hospitals accountable for preventable readmissions, beginning October 2012. Until then, approximately 20% of Medicare patients were readmitted within 30 days of discharge, an excessive number by standards at the Centers for Medicare and Medicaid Services (CMS) (see Kassin, M. T., Owen, R. M., Perez, S., et al. (2012). Risk Factors for 30-Day Hospital Readmission among General Surgery Patients. Journal of the American College of Surgeons, 215(3), 322-330. http://doi.org/10.1016/j.jamcollsurg.2012.05.024). Motivated by the cost of readmission and the poor quality of care indicated, the HRRP strives to incentivize hospitals to implement strategies reducing unnecessary 30-day readmissions. Sepsis accounts for approximately half of hospital deaths, and its treatment costs significantly more than for other high-risk conditions (see Chang, D. W., Tseng, C. H., Shapiro, M. F. (2015). Rehospitalizations following sepsis: Common and costly. Critical Care Medicine, 43(10), 2085-2093. doi: 10.1097/CCM.0000000000001159). A representative study of Americans reported better outpatient care could prevent nearly 40% of sepsis-related readmissions (see Study: Sepsis Readmissions May Be Correctable. (n.d.). Retrieved from http://www.medpagetoday.com/CriticalCare/Sepsis/50415 [16] American Heart Association. (2015 Aug. 5). All about heart rate (pulse). Author. Retrieved from http://www.heart.org/). Sepsis has not received prominent attention at clinical or policy levels under the ACA, despite high mortality rates and excessive healthcare expenditures. Future efforts to reduce hospital readmissions should focus on reducing severe sepsis, as it is largely preventable with improved outpatient care.

Unfortunately, there currently exists no straightforward method to diagnosis sepsis because there is no singular definition, nor a "gold standard" diagnostic test. For over 20 years, the Systemic Inflammatory Response Syndrome (SIRS) criteria have been used to assess sepsis (see Jacob, J. A. (2016). New sepsis diagnostic guidelines shift focus to organ dysfunction. JAMA, 315(8), 739-740. doi:10.1001/jama.2016.0736). SIRS occurs in the presence of two or more of the following criteria: temperature less than 96.8° F. or greater 100.4° F.; respiratory rate greater than 20 breaths per minute; heart rate greater than 90 beats per minute (bpm); and infection, confirmed or suspected (see Comstedt, P., Storgaard, M., & Lassen, A. T. (2009). The Systemic Inflammatory Response Syndrome (SIRS) in acutely hospitalized medical patients: A cohort study. Scandinavian Journal of Trauma, Resuscitation and Emergency Medicine, 17, 67. http://doi.org/10.1186/1757-7241-17-67). While SIRS is related to sepsis, the criteria alone do not necessarily indicate septic organ dysfunction and it can lead to many false diagnoses of sepsis. New guidelines recommend the use of the Sequential Organ Failure Assessment (SOFA) score or the Logistic Organ Dysfunction System (LODS) score to predict mortality for patients in the ICU. These assessments were developed with an updated definition of sepsis as, "an infection that can lead to organ dysfunction" (see Jacob, J. A. (2016). New sepsis diagnostic guidelines shift focus to organ dysfunction. JAMA, 315(8), 739-740. doi:10.1001/jama.2016.0736). Both SOFA and LODS scores leverage clinical and laboratory-obtained measurements, such as coagulation, blood gases, and oxygen level. In a retrospective analysis of ICU-patients with suspected infection, both LODS and SOFA scores had a significantly higher predictive validity in determining patient mortality than SIRS (see Jacob, J. A. (2016). New sepsis diagnostic guidelines shift focus to organ dysfunction. JAMA, 315(8), 739-740. doi: 10.1001/jama.2016.0736). Despite these findings, neither LODS nor SOFA scores can extend beyond the hospital effectively because they require physiological parameters determined by time-consuming laboratory tests.

While SOFA itself does not apply outside of the hospital, a simpler version of it can. Quick SOFA (qSOFA) evaluates only three (3) conditions: 1) altered mental state, 2) systolic blood pressure below 100 mmHg, and 3) respiratory rate elevated above 22 breaths per minute. These requirements constitute a valid approach to swiftly assess sepsis outside of the ICU (see Jacob, J. A. (2016). New sepsis diagnostic guidelines shift focus to organ dysfunction. JAMA, 315(8), 739-740. doi:10.1001/jama.2016.0736). There are, however, several limitations. First, this diagnostic test was developed for and tested on a patient population with suspected infection; thus, qSOFA may not effectively determine the presence of infection (see Seymour, C. W., Liu, V. X., Iwashyna, T. J., et al. (2016). Assessment of clinical criteria for sepsis:

For the third international consensus definitions for sepsis and septic shock (sepsis-3). JAMA, 315(8), 762-774. doi: 10.1001/jama.2016.0288). Additionally, the assessment for altered mental state largely depends on both a clinician and the setting, making it subjective. No studies have yet validated whether qSOFA or SIRS better detects early onset of sepsis in post-surgical, discharged patients. The qSOFA limitations, however, suggest that the score is not entirely relevant to predicting sepsis across this particular patient population. Therefore, adapting sepsis risk indicators to an outpatient, ambulatory setting is a reasonable first step towards reducing sepsis-related hospital readmissions.

SUMMARY

The presently described subject matter is directed to an improved method, system, and apparatus for monitoring a patient for sepsis risk indicators.

The presently described subject matter is directed to an improved method, system, and apparatus for remotely monitoring a patient for sepsis risk indicators.

The presently described subject matter is directed to an improved method, system, and apparatus for remotely monitoring a patient for sepsis risk indicators, and accounting for patient activity in monitoring the patient's risk of sepsis in a manner to reduce the false positive rate.

The presently described subject matter is directed to an improved method, system, and apparatus for remotely monitoring a patient for sepsis risk indicators, determining the patient's risk of sepsis, and accounting for patient activity in the determination of the patient's risk of sepsis in a manner to reduce the false positive rate.

The presently described subject matter is directed to a method for remote monitoring a patient for sepsis risk indicators, comprising or consisting of provisioning the patient with a wearable biometric sensor capable of detecting variables such as heart rate, respiratory rate, and activity or acceleration; detecting the variables of the patient by the biometric sensor; generating a wireless signal comprising the detected variables by the biometric sensor; communicating the wireless signal from the biometric sensor to a mobile phone or a mobile application; measuring variables such as temperature and blood pressure of the patient; inputting the measured variables into the mobile phone or the mobile application; communicating a mobile signal comprising the detected variables and measured variables from the cell phone or cell platform to a server; receiving the mobile signal at a remote location; determining the patient's risk of sepsis using the detected variables and measured variables; and accounting for patient activity in the determination of the patient's risk of sepsis in a manner to reduce a false positive rate.

The presently described subject matter is directed to the above method for remote monitoring a patient for sepsis risk indicators, further comprising or consisting of distinguishing between physical activity-related elevation of vital signs and sepsis-related elevation of the vital signs.

The presently described subject matter is directed to the above method for remote monitoring a patient for sepsis risk indicators, further comprising or consisting of distinguishing between physical activity-related elevation of vital signs and sepsis-related elevation of the vital signs; and accounting for physical activity-related elevation of vital signs in determining the patient's risk of sepsis.

The presently described subject matter is directed to the above method for remote monitoring a patient for sepsis risk indicators, further comprising or consisting of distinguishing between physical activity-related elevation of vital signs and sepsis-related elevation of the vital signs; accounting for physical activity-related elevation of vital signs in determining the patient's risk of sepsis; and diagnosing and treating the patient to reduce the patient's risk of developing sepsis.

The presently described subject matter is directed to the above method for remote monitoring a patient for sepsis risk indicators, wherein a server receives the mobile signal.

The presently described subject matter is directed to the above method for remote monitoring a patient for sepsis risk indicators, wherein a server receives the mobile signal, and wherein the server is a cloud server.

The presently described subject matter is directed to the above method for remote monitoring a patient for sepsis risk indicators, wherein the detected values are continuously monitored and patient activity is tracked in a manner to detect early warning signs of sepsis and allow for more timely interventions to reduce unnecessary readmissions and improve mortality rates.

The presently described subject matter is directed to the above method for remote monitoring a patient for sepsis risk indicators, wherein the measured values are measured at least once per day.

The presently described subject matter is directed to the above method for remote monitoring a patient for sepsis risk indicators, wherein the detected values are continuously monitored and patient activity is tracked in a manner to detect early warning signs of sepsis and allow for more timely interventions to reduce unnecessary readmissions and improve mortality rates, wherein the measured values are measured at least once per day.

The presently described subject matter is directed to the above method for remote monitoring a patient for sepsis risk indicators, wherein a server receives the mobile signal, and wherein the server determines the patient's risk of sepsis.

The presently described subject matter is directed to the above method for remote monitoring a patient for sepsis risk indicators, wherein a server receives the mobile signal, wherein the server determines the patient's risk of sepsis; and wherein the server uses data from the biometric sensor to mask out time periods where heart rate, respiratory rate, temperature, and blood pressure data are likely to have been affected by intense physical activity to preclude a false positive indication.

The presently described subject matter is directed to the above method for remote monitoring a patient for sepsis risk indicators, wherein a server receives the mobile signal, and wherein the server determines the patient's risk of sepsis, and wherein the server calculates the patient's risk of sepsis using an algorithm.

The presently described subject matter is directed to the above method for remote monitoring a patient for sepsis risk indicators, wherein a server receives the mobile signal, and wherein the server determines the patient's risk of sepsis, wherein the server calculates the patient's risk of sepsis using an algorithm, and wherein the algorithm is configured to take into account current clinically-accepted techniques used to assess sepsis.

The presently described subject matter is directed to the above method for remote monitoring a patient for sepsis risk indicators, wherein a server receives the mobile signal, and wherein the server determines the patient's risk of sepsis, wherein the server calculates the patient's risk of sepsis using an algorithm, and wherein the calculation is according to the following algorithm:

Heart Rate
  If average heart rate is <½ (220-age) bpm, then flag is O,
  If average heart rate is >½ (220-age) bpm AND
  Activity is 1, then flag is O,
  Activity is 0, then flag is 1,
    wherein average heart rate is average heart rate over the last 15 minutes with no flag is thrown in first 15 minutes,
Respiratory Rate
  If average respiratory rate is between 8-22 bpm, then flag is 0,
  If average respiratory rate is <8 bpm, then flag is 1,
  If average respiratory rate is >22 bpm AND
  Activity is 1, then flag is 0
  Active is 0, then flag is 1;
    wherein average respiratory rate is average breathing rate over the last 15 minutes with no flag thrown in first 15 minutes,
Temperature and Blood Pressure
  If temperature is between 96.8 F-100.4 F, then flag is 0,
  If temperature is below 96.8 F or greater than 100.4 F, then flag is 1,
    wherein, if activity is within last 30 minutes, delay prompt by 30 minutes,
Suspected Infection
  If 1+ major symptom is checked in checklist, then flag is 1,
  If 2+ minor symptoms are checked in checklist, then flag is 1,
    wherein, checklist includes fever, diarrhea, and vomiting, and
Activity
  If accelerometer values peak 2 standard deviations (Stdev) from average noise level or heat rate (HR) is >50% of maximum AND
    Vitals peak 10-60 seconds or more than 5 minutes, then flag is 0,
    Vitals above 50% of maximum from 1-5 minutes, then flag is 1,
  If accelerometer values <2 Stdev from average noise level or HR is <50% of maximum, then flag is 0.

The presently described subject matter is directed to the above method for remote monitoring a patient for sepsis risk indicators, wherein a server receives the mobile signal, and wherein the server determines the patient's risk of sepsis, wherein the server calculates the patient's risk of sepsis using an algorithm, wherein the algorithm is configured to take into account current clinically-accepted techniques used to assess sepsis, and wherein the patient is prompted to confirm activity, if accelerometer values peak 2 standard deviations (Stdev) from average noise level or heat rate (HR) is >50% of maximum.

DETAILED DESCRIPTION OF DRAWINGS

FIG. 1 is a diagrammatic view of an algorithm for determining a patient's risk of sepsis.

FIG. 5 is a table showing challenges associated with remote monitoring a patient for sepsis.

FIG. 8 is a functional block diagram for a computer system for implementation of an exemplary embodiment or portion of an embodiment of the present invention.

DETAILED DESCRIPTION

This invention provides a method, system, and apparatus for translating ICU scoring systems of sepsis risk to the ambulatory setting by monitoring outpatient populations using an algorithm that detects subtle changes in the sepsis risk indicators of heart rate, respiratory rate, temperature, blood pressure, and suspected infection.

Since patient activity and exercise can elevate vitals and confound sepsis risk variables, the algorithm accounts for patient activity in determining whether a patient is at risk for sepsis. In an ambulatory setting, detecting changes in patient vitals and providing daily generated reports will enable patient care coordinators to better diagnose and determine the best course of action for patients at risk of developing sepsis.

This invention involves the provisioning of discharged patients with a wearable biometric sensor (or sensors) capable of detecting variables such as heart rate, respiratory rate, and acceleration. Sepsis risk indicators that cannot be detected by the sensor are measured via user input on a mobile application. The sensor measurements are sent via wireless signaling to a mobile phone or other mobile platform, which then sends both the raw, continuous values and user inputs to a cloud server that calculates patient risk based on an algorithm that takes into account current clinically-accepted techniques used to assess sepsis in hospitals, with the key step being a method for distinguishing between physical activity-related elevation of vital signs and sepsis-related elevation of vital signs. The algorithm is shown in FIG. 1.

Figure 2:
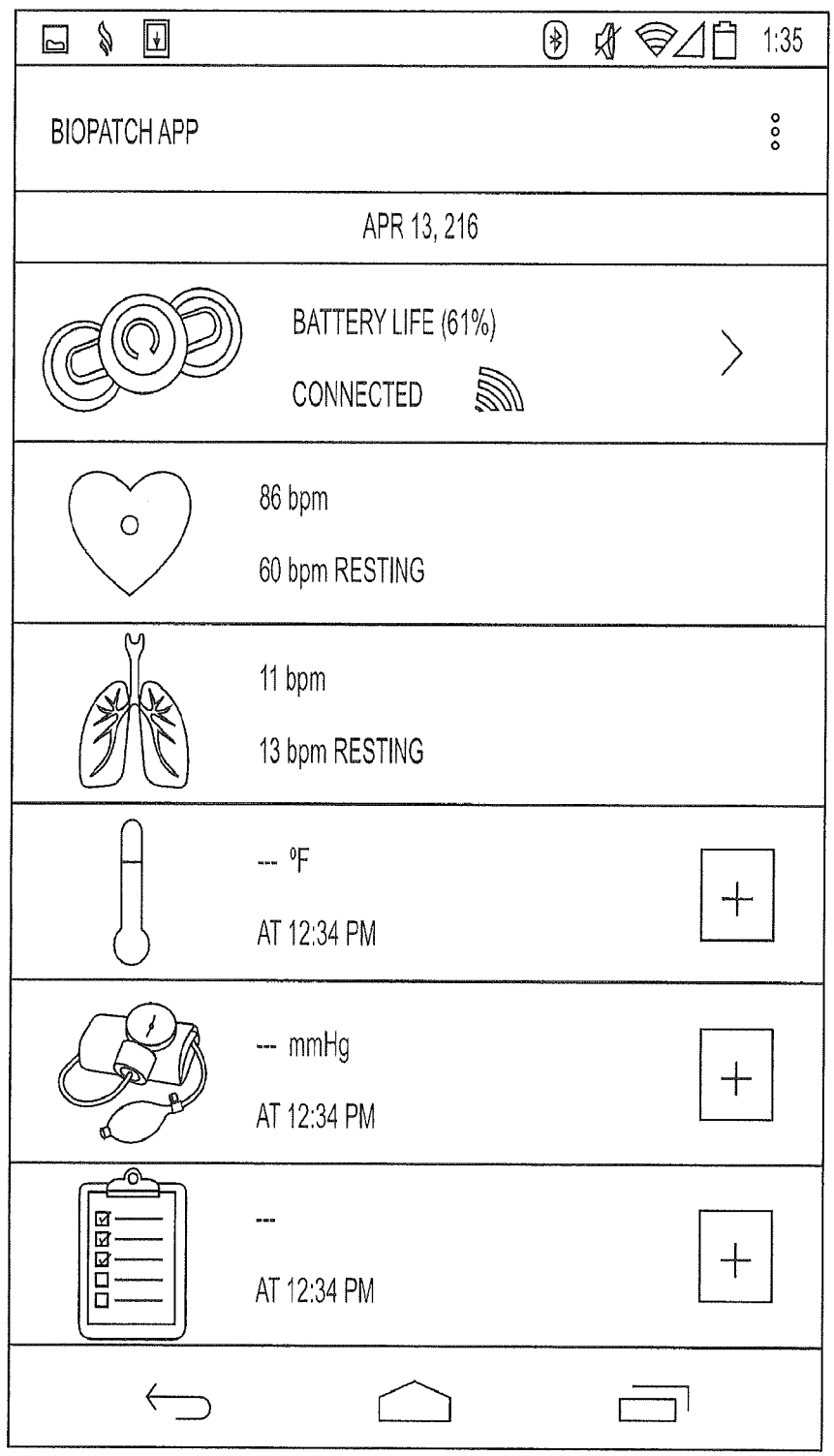
FIG. 2 is a screen shot of a mobile application according to the present invention showing a patient's vital signs for determining a patient's risk of sepsis.
Figure 3:
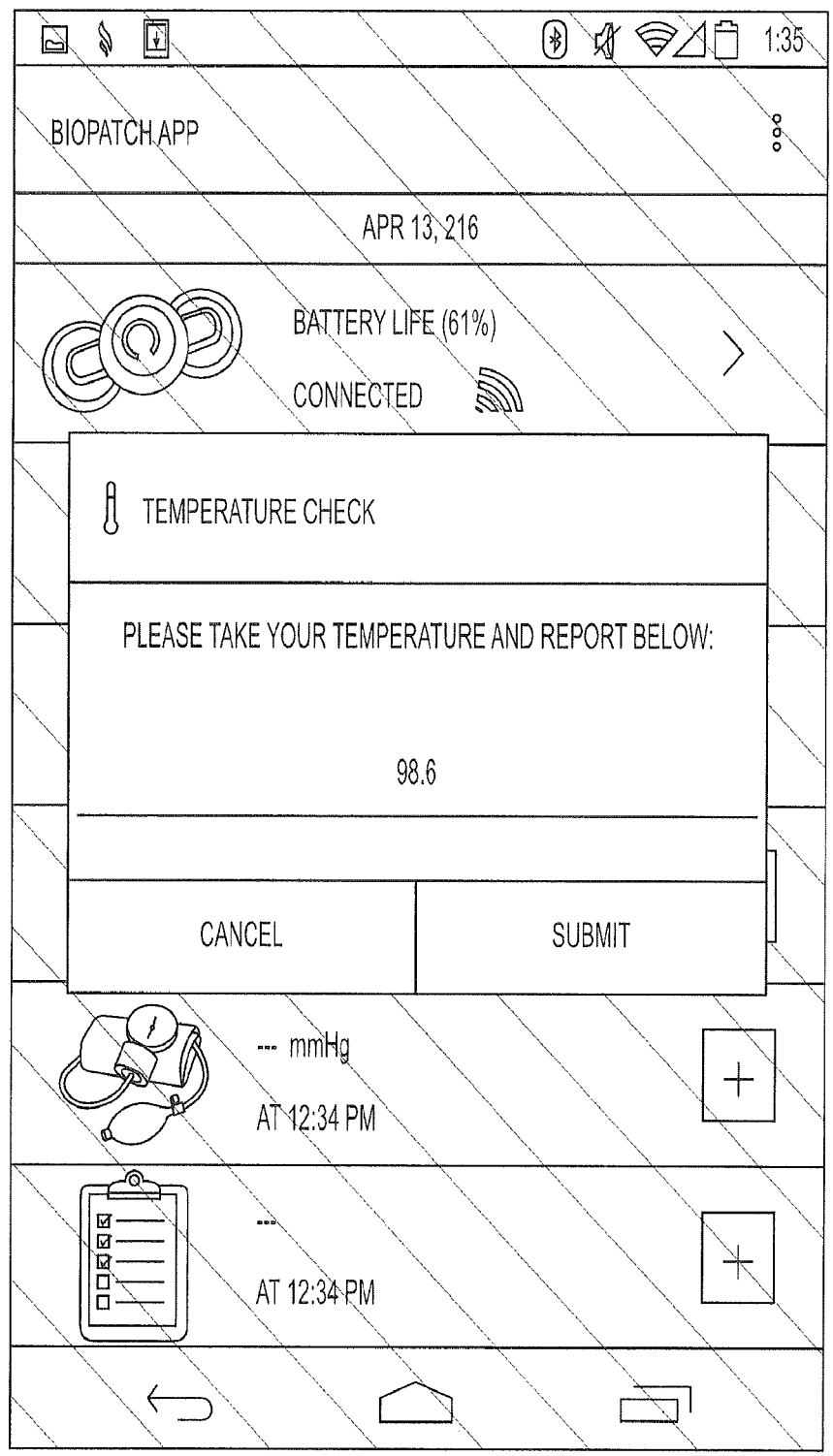
FIG. 3 is a screen shot of a mobile application according to the present invention showing a patient prompt to enter the patient's temperature.
Figure 4:
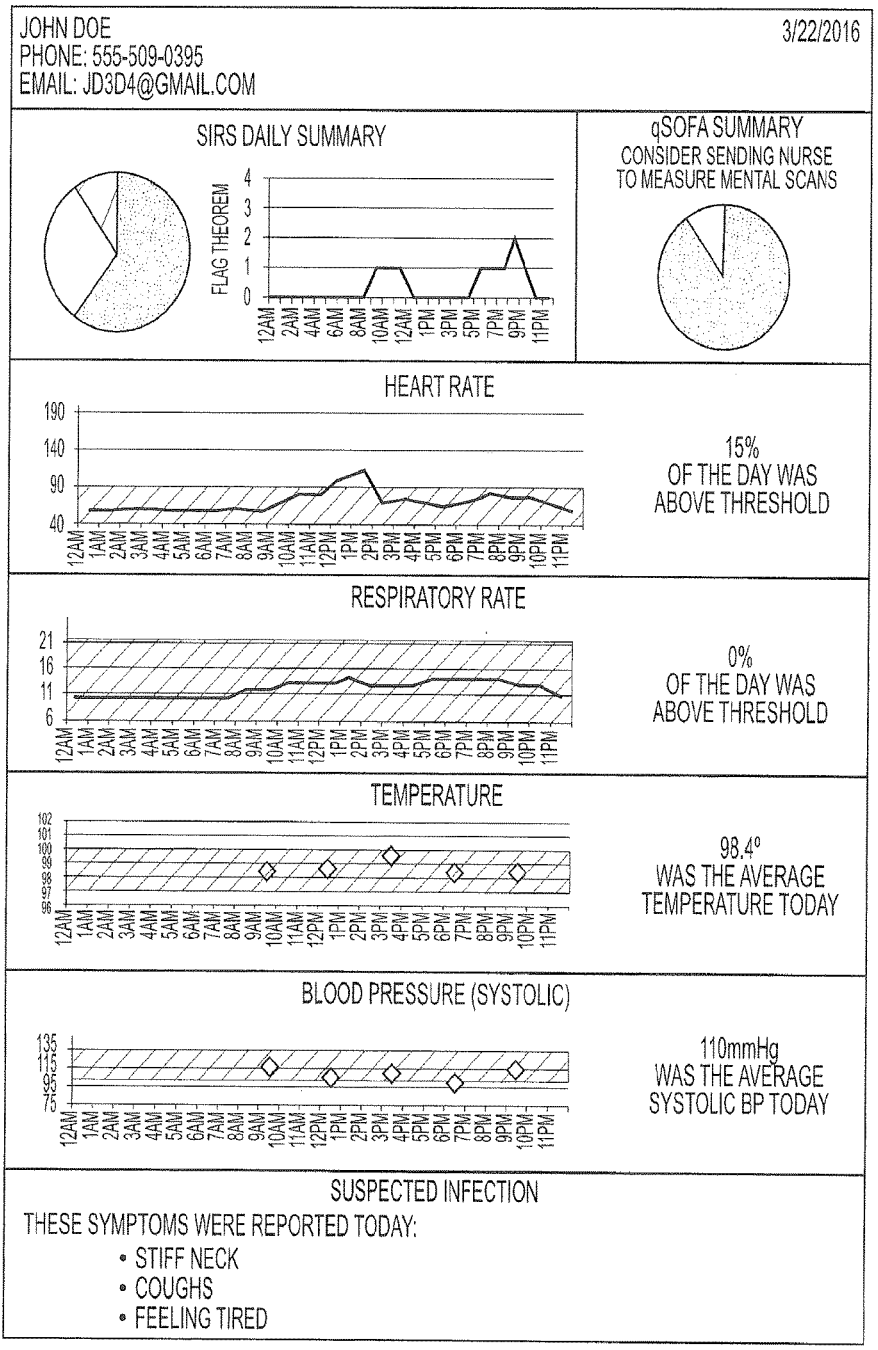
FIG. 4 is a dashboard presentation showing percentages over the previous day for a number of sepsis-related indicators or markers.
Figure 6:
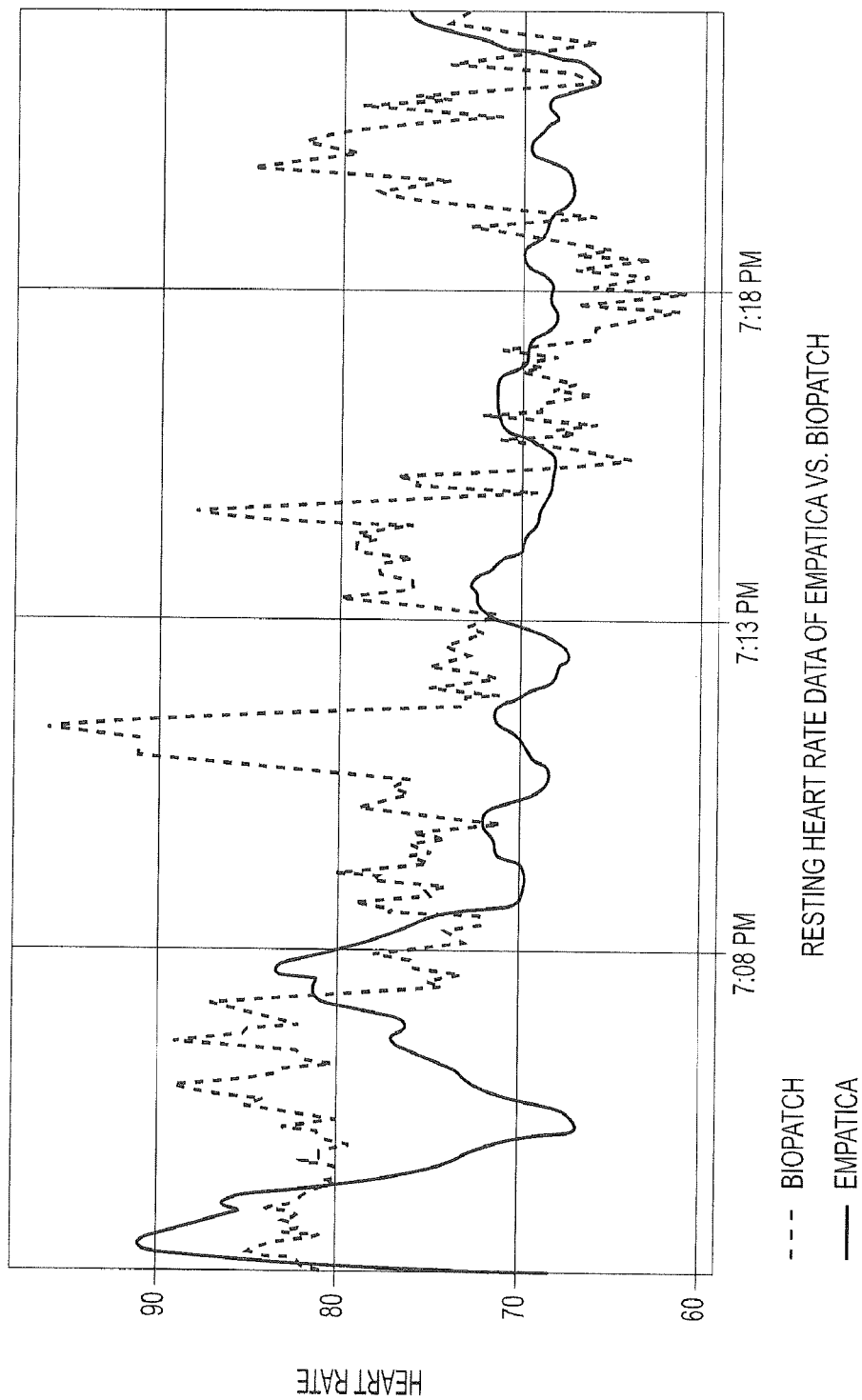
FIG. 6 is a graph of the resting heart rate verses time for resting heart rate data of Empatica vs. BioPatch.

The screen shots of the mobile application is shown in FIGS. 2 and 3. This application is a specific application of the methodology. As an end-to-end method, system, and apparatus, this system ultimately prepares a daily report (for use either by physicians or clinical care coordinators) providing a dashboard presentation showing percentages of the previous day over different numbers of sepsis-related markers were present. See FIG. 4.

Again, the key step here is the use of physical activity and heart-rate sensor data (FIG. 1) to "mask" out time-periods where heart-rate, respiratory rate, temperature, and blood pressure data are likely to have been affected by intense physical activity.

Currently, there are very few remote patient monitoring solutions that focus on sepsis risk detection. Furthermore, those that do exist do not take into account patient activity, which may lead to more false positive cases. Discerning patient activity is necessary for translating these hospital risk assessments to the ambulatory setting because patient vitals, like heart rate, behave differently while a patient is immobile (e.g. in a hospital bed) than they may at home where a patient is less restricted in terms of movement. Thus, hospital assessments for sepsis would trigger numerous false-positives in the at-home setting because patient vitals (like heart and breathing rate) naturally elevate during activity.

Continuous monitoring for variations in patient vitals while tracking activity could detect early warning signs of sepsis and allow for more timely interventions to help to reduce unnecessary readmissions and improve mortality rates. Remote monitoring is particularly useful in ambulatory settings for supervised recovery from surgery, as the patient would not be encumbered by intrusive equipment.

No existing methodology for remote patient monitoring of sepsis is as robust as the proposed methodology.

Design Considerations

Remote patient monitoring solutions enable a more preventative approach to medicine, augmenting current medical efforts that focus primarily on reactive treatments and management of disease. Continuous monitoring for slight variations in patient vitals could detect early warning signs of sepsis and allow for more timely interventions to help to reduce unnecessary readmissions and improve mortality rates (see Stopping Sepsis in its Tracks [Web log post]. (n.d.). Retrieved from http://www.isansys.com/content2012/display_news.php=27). Remote monitoring is particularly useful in ambulatory settings for supervised recovery from surgery, as the patient would not be encumbered by intrusive equipment (see Otto, C., Milenković, A., Sanders, C., et al. (2006). System architecture of a wireless body area sensor network for ubiquitous health monitoring. Journal of Mobile Multimedia, 1(4), 307-326). Although remote monitoring can be an inexpensive and relatively accurate way to monitor patient health outside of the hospital, it faces significant challenges before it can be implemented effectively.

I. Discerning Patient Activity

Patient mobility distinguishes the hospital and home environments in that the ICU typically restricts patient movement in ways the home does not. In order to effectively monitor for sepsis in the outpatient population, exercise is a key component to be weighed with the traditional benchmarks.

A remote monitoring system for sepsis detection outside the ICU must account for the patient's activity. The system could incorrectly indicate a problem state in a setting where individuals are allowed free range of motion because heart rate and other vital signs are generally elevated during physical activity. Since heart rate reacts gradually to activity, monitoring for changes in this vital sign provides a method for distinguishing between patients who are moving and those who are sedentary (see Tapia, E. M., Intille, S. S., Haskell, et al. (2007, October). Real-time recognition of physical activities and their intensities using wireless accelerometers and a heart rate monitor. 2007 11th IEEE International Symposium on Wearable Computers, 37-40). In addition to vital sign data, the accelerometer is the most commonly used sensory device to capture human activity for assessment (see Khan, A. M., Siddiqi, M. H., & Lee, S-W. (2013). Exploratory data analysis of acceleration signals to select light-weight and accurate features for real-time activity recognition on smartphones. Sensors, 13, 13099-13122). Accelerometers give a spatial understanding of the user's movements in all three dimensions. Many researchers have effectively utilized accelerometers to classify human activity with machine learning techniques (see Bayat, A., Pomplun, M., & Tran, D. A. (2014). A study on human activity recognition using accelerometer data from smartphones. Procedia Computer Science, 34, 450-457, see González, S., Sedano, J., Villar, J. R., Corchado, E., Herrero, Á., & Baruque, B. (2015). Features and models for human activity recognition. Neurocomputing, 167, 52-60, see Lara, Ó. D., Pérez, A. J., Labrador, M. A., et al. (2012). Centinela: A human activity recognition system based on acceleration and vital sign data. Pervasive and Mobile Computing, 8, 717-729). Another method for automated exercise detection uses step intensity segmentation, which is currently featured in commercially available fitness trackers such as the Fitbit and Jawbone (see Goode, L. (2015 Nov. 23). Your Fitbit now automatically knows when you're exercising. The Verge. Retrieved from http://www.theverge.com/2015/11/23/9779512/your-fitbit-now-automatically-knows-when-youre-exercising, see Nomura, E. & Wilt, B. (2014 Nov. 4). Smart coach: Getting to know your workout. Jawbone. Retrieved from https://jawbone.com/blog/workout-tracking/).

Two main characterizations of activity are apparent from previous efforts: intensity and duration. The peaks in accelerometer and vital sign data correspond with bursts of exertion, potentially caused by physical activity or arousal. Long and very short peaks augment the intensity measures by excluding normal periods of exercise that are generally not life-threatening. Both the intensity and the duration of sensory data spikes should be evaluated for abnormalities, which can provide more insight into a patient's health. Since discharged patients are not limited to the bedside, a robust sepsis-monitoring system must account for the possibility of increased movement.

II. Baselining Vitals

The home setting removes the omnipresence of medical care, presenting a challenge for remote monitoring systems because these environments lack the clinical supervision of nurses and doctors. Since each patient is unique, his or her vitals and behavior will not necessarily follow textbook profiles. Medical professionals can compensate for this by using intuitive evaluation and patient medical records to discern abnormal patient behavior. To be clinically effective, a remote monitoring system should provide the same level of unique care to each patient.

Baselining is particularly challenging with regards to heart rate. While the average resting heart rate is 60-100 bpm, this range is not specific enough for effective sepsis monitoring (see American Heart Association. (2015 Aug. 5). All about heart rate (pulse). Author. Retrieved from http://www.heart.org/). Currently, commercially available heart rate monitors like the Fitbit ChargeHR determine users' resting heart rates when they sleep because the heart rate is not masked by other variables like activity (see Fitbit, Inc. (2016). What should I know about my heart rate data? Author. Retrieved from http://help.fitbit.com/articles/en_US/Help_article/Heartrate-FAQs/?!=en_US&c=Topics%3AFAQs&p=charge_hr&fs=Search&pn=1#Restin gMeasured). For exercise tracking, the system can wait until the user sleeps to determine the resting heart rate because the information has no urgency. However, remote patient monitoring requires the resting heart rate upon deployment so that it can recognize elevated heart rate levels. Hospitals gather patients' vital information during their stay and that information could feed a remote monitoring system with a specific resting heart rate immediately. The age of the patient can also help to determine a patient's baseline vitals if the value is unavailable at the hospital. The American Heart Association (AHA) states that maximum heart rate declines as age increases. Subtracting one's age from 220 bpm gives the approximate maximum heart rate; the heart should not exceed half of the maximum heart rate if a person is not exercising (see American Heart Association. (2016 Jan. 13). Target heart rates. Author. Retrieved from http://www.heart.org/). The simplicity of this method makes it viable for use in a sepsis-monitoring monitoring system. Other indicators of sepsis, including respiratory rate and temperature, do not vary as much throughout the general population. For instance, average respiratory rate is between 8-20 breaths per minute, and average core body temperature is widely known to be 98.6° F. However, if a patient's vitals naturally deviate from these rule-of-thumb ranges, then the system should account for those variances. Individualizing a sepsis-monitoring system will provide deeper insight into abnormal patient behavior, enabling more effective detection of sepsis.

III. Patient Involvement and Compliance

Monitoring sepsis risk indicators in a home setting is challenging because it relies heavily on patient compliance. Although many biometric devices can collect continuous data on certain vitals, the user needs to report other variables directly. Many remote monitoring systems fail to consider the social aspects of patient adherence (see Rezai, L. S., Torenvliet, G., & Burns, C. M. (2014). Increasing patient adherence to home health-monitoring systems. Proceedings of the International Symposium on Human Factors and Ergonomics in Health Care, 3(1), 8-14). An effective remote monitoring system for early indication of sepsis should consider proper compliance strategies, information display theory, and approaches to data collection.

The frequency of information collection influences patient compliance. The design must balance between overwhelming the user and receiving enough information to be useful. However, no consistent guideline exists for how often to measure vitals. For patients in a hospital environment, the World Health Organization (WHO) recommends temperature measurements every six hours after admission for sepsis, and one to three times daily after the first 24 hours (see Asiimwe, S., Okello, S., & Moore, C. (2014). Frequency of Vital Signs Monitoring and its Association with Mortality among Adults with Severe Sepsis Admitted to a General Medical Ward in Uganda. PLoS ONE, 9(2)). Since a fever can take up to 60 minutes to develop, failing to probe this often could lead to a delayed detection of sepsis (see Z, M. (1999). How does the immune system communicate with the brain? Neurol Neurochir Pol, 33(3)). For ambulatory settings, healthcare programs established "track and trigger" systems that set the frequency of vital monitoring based on changes in vital sign thresholds and triggers (see Berwick, D. M., Hackbarth, A. D., & McCannon, C. J. (2006). IHI replies to "The 100,000 Lives Campaign: A scientific and policy review. Joint Commission journal on quality and patient safety, 32(11), 628-30).

Additionally, the presentation of information should carefully consider post-operative patients and their involvement in monitoring their own health. Patients tend to engage more when they can see their health statistics (see Wilcox, L., Morris, D., Tan, D., et al. (2010). Designing patient-centric information displays for hospitals. Proceedings of the 28th International Conference on Human Factors in Computing Systems—CHI '10). In an ambulatory setting, a display of patient vitals should provide enough information for patients to understand their health and know when a significant change occurs. Therefore, patient adherence and compliance will improve with careful consideration of how often to probe patients for information and of how to display that information.

IV. Quality of Biometric Devices

In the hospital setting, an industry-standard device often monitors patients' vitals. To detect heart rate and rhythm, hospitals typically use the Holter monitor, considered the "gold standard" for electrocardiogram (ECG) measurements. However, no clear-cut standard device exists for measuring vitals or detecting sepsis since remote monitoring technology is a relatively new field. The market for wearable biometric devices has a wide range concerning the type, method, and frequency of data collection. Many fitness trackers, such as the Fitbit SURGE, allow for limited data collection, such as heart rate and step count. While sufficient for activity, such monitors are inadequate for early sepsis detection, which requires temperature and breathing rate as well.

The method of data collection is critical. A study on signal quality for wireless monitoring found photoplethysmography (PPG) sensors to be more "morphologically variable" than ECG sensors (see Orphanidou, C., Bonnici, T., Charlton, P., et al. (2015). Signal-quality indices for the electrocardiogram and photoplethysmogram: Derivation and applications to wireless monitoring. IEEE Journal of Biomedical and Health Informatics. 19(3), 832-838 [24]). The frequency of data collection varies, with a higher rate correlating to more discretized data information. While both devices have FDA approval, the Zephyr BioPatch samples ECG data at a rate of 250 Hz compared to the Empatica E4 at a rate of 64 Hz (see Garbarino, M., Lai, M, Bender, D., et al. (2014). Empatica E3-A wearable wireless multi-sensor device for real-time computerized biofeedback and data acquisition. 2014 EAI $4^{th}$, International Conference on Wireless Mobile Communication and Healthcare. 39-42, see Zephyr. (2016). Development Tools. Retrieved from http://www.zephyr-technology.nl/en/article/54/development-tools.html). Each of these factors contributes to the usability of biometric devices.

In addition to data quality, federal device approval and data ownership are critical factors that must be considered. Although commercial devices may meet the requirements of collecting the right amount of data at an appropriate frequency, U.S. Food and Drug Administration (FDA) must approve these devices to be adequate for early sepsis monitoring. Furthermore, several devices retain ownership of biometric information collected. For example, the Hexoskin API terms and conditions state, "you do not acquire ownership of . . . the content that is accessed through our APIs" (see Hexoskin. (2016). Hexoskin APIs terms of service. Retrieved from https://api.hexoskin.com.docs/page/terms-and-conditions/). Another consideration is the ability to access and interpret data, which is essential for any home-grown system. Ultimately, only devices, which are federally approved, do not retain data ownership, and have data which can be obtained and manipulated, can be included in an early sepsis detection system.

V. Communicating Findings to Care Coordinators

Since patient care coordinators are responsible for overseeing many patients simultaneously, it is important to consider how patient vital information is presented to them. With the patient population living in an ambulatory, home setting, multiple positive indicators of sepsis may be detected throughout the day. Sending notifications to care coordinators each time one of their patients exhibits multiple sepsis risk indicators could overwhelm coordinators and distract from their daily workflow. Alarm fatigue, a state in which care coordinators become desensitized to a notification or alarm, is common in the healthcare community, which can lead to missed events and result in lower quality of care (see Sendelbach, S. (2012). Alarm fatigue. Nursing Clinics of North America, 47(3), 375-382. doi:10.1016/j.cnur.2012.05.009). Any system that produces notifications inherently becomes prescriptive, as it informs the care coordinators that an event has occurred. By defining an event, the expertise implicitly shifts from the doctors to the system designers. As such, notifications should only convey the detection of critical patient conditions. As an alternative to an alert-based system, generated reports from the system provide summaries highlighting certain patient information collected throughout the day. Presenting information once daily mitigates the issue of alarm fatigue. Designers may have to act as decision-makers to decide on the displayed information; however, this alternative is significantly less prescriptive in nature than an alert-based system. By presenting patient data in such a format, medical professionals can make their own judgments on necessary further actions.

System

Considering challenges associated with remote monitoring for sepsis, summarized in FIG. 5, we developed an algorithm that marks severe changes in the sepsis risk indicators of heart rate, respiratory rate, temperature, blood pressure, and suspected infection, which then generates a daily report for the patient care coordinator. Using this report, care coordinators can make informed decisions about how to best respond to dynamic outpatient care.

I. Sensors

The proposed system will continuously monitor the heart and respiratory rate of the user. High-frequency sensory devices can have occasional outliers, which could inaccurately suggest a patient is outside of the appropriate health range. Therefore, to reduce the false positive rate, a 15-minute moving average is used for both heart and respiratory rates. A normal value for breathing rate will be in the range of 8 to 22 breaths per minute. Breathing rates below 8 or above 22 breaths per minute are considered abnormal, which will be marked in the system as meeting one of the criteria for indication of sepsis. However, additional analysis and processing should be conducted for elevated vitals, since increased levels can also be attributed to physical activity.

Unusual patterns in the patient's accelerometer data for intensity and duration should be taken into account in the home setting, since the patient's mobility is not as restricted. The accelerometer data will be aggregated into relative distance measurements between points across the three (3) axes over time. Spatial data can be classified as abnormal if it is above two standard deviations away from the average noise level of the sensor, which covers approximately 95% of events assuming a normal distribution. The sensory device will have a base level of noise in the data, so the range will account for these random variations. Intensity can also be benchmarked with heart rate, as a person's heart rate should be within fifty to eighty-five percent range of his or her maximum heart rate during exercise (see American Heart Association. (2016 Jan. 13). Target heart rates. Author. Retrieved from http://www.heart.org/). Therefore, a person's heart rate can be considered abnormal if it is greater than half of the difference between 220 beats per minute and age.

Additionally, very short, sustained heart rate peaks of under a minute in duration beyond the threshold could indicate an arrhythmia or other health concerns. Conversely, long durations of ten minutes or more can be problematic, as vitals should return to baseline within a few minutes after exercise (see Sinha, R. (2013 Mar. 19). Get to know your heart rate—It might save your life. Prevention & Wellness. In Palo Alto Medical Foundation Health Blog. Retrieved from http://www.pamfblog.org/2013/03/know-your-heart-rate/). When long or very short peaks are found, a prompt will ask the patient to confirm the exercise. If the person does not respond or confirm exercise, then the system notes the period as a problematic event. Otherwise, if it is indicated, then patient vitals are ignored for that time period.

II. User Prompts

Unlike measurements for heart and respiratory rate, the remaining sepsis risk indicators of temperature, blood pressure, and suspected infection cannot be measured automatically using accessible, commercially-available devices. Therefore, the system will probe the patient for an update on their vitals once each day to encourage patient compliance. If activity has been detected within the last 30 minutes, the prompt will be delayed by that amount of time in order to avoid discrepancies from activity. Furthermore, users who are interested in providing care coordinators with more information can choose to input their temperature, blood pressure, and symptoms at any point during the day.

At noon, the system will ask the user to use a skin thermometer to measure their temperature. If the temperature is less than 96.8° F. or greater than 100.4° F., the system marks this data point as extreme. Once the temperature is entered, the system will then ask the user to measure their blood pressure with a blood pressure cuff. If their systolic blood pressure is 100 mm Hg or less, the variable is marked as abnormal. After both temperature and blood pressure are measured, the user will be asked if he or she experienced any symptoms of infection in the last 24 hours. If the user has felt symptoms of infection, the person can mark major and minor symptoms from a checklist. If one major symptom or two minor symptoms are met for the day, the system will report that there were abnormal patient symptoms.

II. Generated Report

The patient reports will allow care-coordinators to view summary information of patients' biometrics from the past 24 hours. Reports are generated either on demand or by 1 p.m. for the care-coordinator to have sufficient time to act on the given information before the business day ends. The report will have a daily review section, which provides a summary of how many vital signs exhibited abnormal behavior throughout the day.

Beyond the summary statistics, the report will provide more detailed information on each of the sepsis risk indicators. Since heart rate and respiratory rate are measured continuously, they can be summarized in time series plots. Since temperature and blood pressure are provided by the user, these graphs will only display discrete point values over time. Each of the graphs will display thresholds for abnormal measurements based on SIRS and qSOFA criteria. Sections which meet the above definition of activity are not included on the graph, since activity contributes to elevated vitals. The percentages of time during the day the thresholds are exceeded during a time of non-activity will be displayed adjacent to the corresponding graphs. For suspected infection, the report will reflect the symptoms reported by the patient in the last 24 hours.

Prototype

I. Monitoring Device Comparison

Doctors at the Scripps Institute conducted a head-to-head study of patch heart monitors against the Holter monitor and found that the patch detected more events than the Holter monitor (see Barrett, P. M., Encinas, J., Fought, A. J., et al. (2014). Comparison of 24-hour Holter monitoring with 14-day novel adhesive patch electrocardiographic monitoring. *The American Journal of Medicine*, 127(1):95.e11-7. doi:10.1016/j.amjmed.2013.10.003). Similarly, we ran a head-to-head study on the Zephyr BioPatch and the Empatica E4 wrist band with FIG. 1 displaying the resulting time-series graph over 12 minutes while the user was at rest with both devices.

Although there is a clear discrepancy between the two devices, there is insufficient evidence to justify the accuracy of one device over the other.

II. System Design

Figure 7:
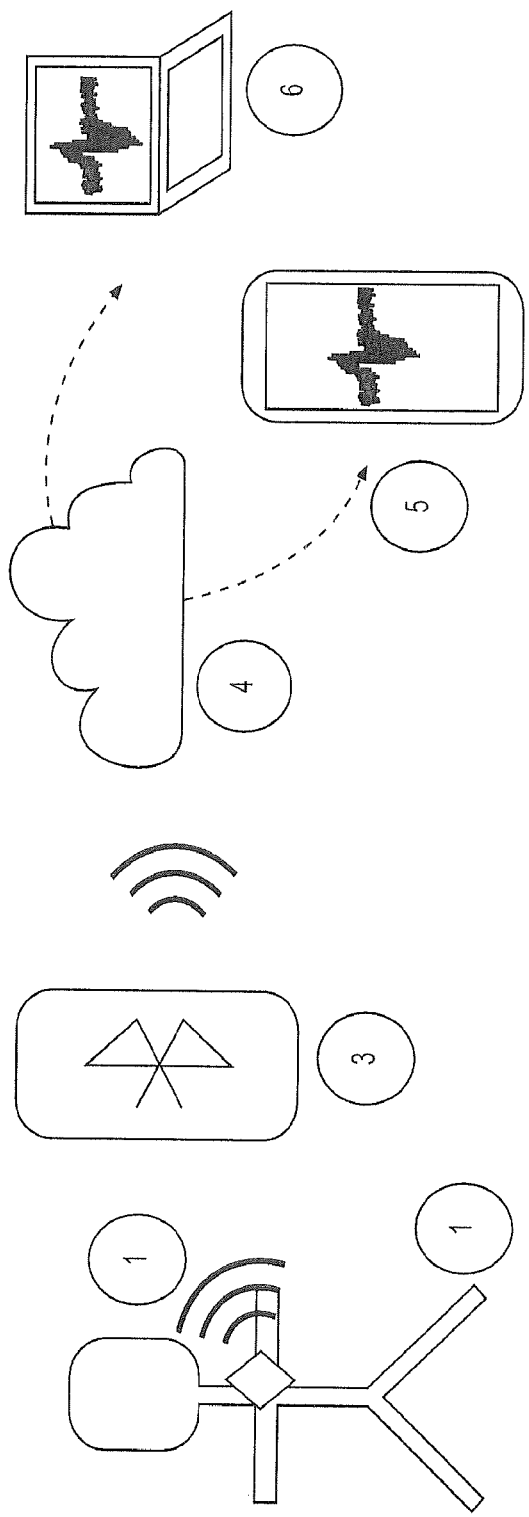
FIG. 7 is a diagrammatic view of a system according to the present invention.

The prototype design, as depicted in FIG. 7, implements the Zephyr BioPatch 1, a prescription-grade Class 2 FDA approved device, which is manually applied to a person's chest 2 with two adhesive electrodes. The single-lead ECG device samples an ECG waveform at a rate of 250 Hz; acceleration at 100 Hz; and heart rate and respiratory rate at 1 Hz. A manual thermometer and blood cuff are used to collect data because the BioPatch does not currently support temperature or blood pressure monitoring. In addition to being appropriate in terms of data quality, the BioPatch has an open API; does not retain ownership of biometric information; and is approved by the FDA.

Biometric information transmits from the BioPatch to an Android device via a Bluetooth connection through a developed Android application 3. From the application, biometric information streams to a cloud-based database, Microsoft Azure 4, which stores data on a SQL server. Information is retrieved on a password-protected web application since each biometric data sequence stores an individual's identity that was entered into the Android device 5. The Azure-based web application stores individual biometric information, which is then aggregated to generate a daily report for the care coordinator 6.

DISCUSSION

Although remote monitoring provides a valid first attempt at detecting signs of sepsis for the outpatient community, there are limitations to this proposed system. A primary limitation is the fact that the system has yet to be fully developed, and as such, there is no data to support claims, such as the ability to distinguish activity. Furthermore, the underlying Gaussian assumption for activity may not be supported. Provided that the system operates reliably, there are still concerns related to the validity of SIRS and qSOFA criteria predicting sepsis in the outpatient setting. One focus of discussion distinguishes the criteria from an actual condition to be treated. The benchmarks should prompt physicians to investigate the underlying causes and not merely treat symptoms [32]. Further concerns include the restriction that temperature and blood pressure are only discretely collected, which cannot account for sudden changes in these vitals. The system also relies heavily on proper user compliance, which may present issues of accurate data collection and input. The system is also not currently compatible with operating systems other than Android devices, which excludes a significant portion of the outpatient population. Finally, given the unclear results obtained in the head-to-head study of the two biometric devices, a new study will introduce an additional sensor, the Fitbit Charge HR, to validate the device used in the proposed system. Results are expected by the middle of April 2016.

A pilot deployment of the remote monitoring system seeks to provide data and insight into the potential of extension of the SIRS criteria and qSOFA into the home as a solution for reducing readmissions and improving quality of care of discharged patients. While data on patients' risk for sepsis in the hospital exists, there is currently no data on outpatient risk that provides conclusive evidence toward the effectiveness of remote monitoring for sepsis at home. The proposed solution is the first iteration of a remote monitoring system designed to be robust and personalized for early detection of sepsis outside the hospital.

Effective monitoring of sepsis can reduce readmission costs for hospitals, since Medicare reports that a large percentage of readmissions are preventable. Insufficient knowledge and improper training for postoperative care of discharged patients further enhances the importance of sepsis monitoring at home. Thus, the system may be prescribed to postoperative, discharged patients who are at increased risk for sepsis. The remote monitoring algorithm would enable patient care coordinators to better monitor their patients for signs of sepsis.

FIG. 8 shows a functional block diagram for a computer system 500 for implementation of an exemplary embodiment or portion of an embodiment of present invention. For example, a method or system of an embodiment of the present invention may be implemented using hardware, software or a combination thereof and may be implemented in one or more computer systems or other processing systems, such as personal digit assistants (PDAs) equipped with adequate memory and processing capabilities. In an example embodiment, the invention was implemented in software running on a general purpose computer 50 as illustrated in FIG. 8. The computer system 500 may include one or more processors, such as processor 504. The processor 504 is connected to a communication infrastructure 506 (e.g., a communications bus, cross-over bar, or network). The computer system 500 may include a display interface 502 that forwards graphics, text, and/or other data from the communication infrastructure 506 (or from a frame buffer not shown) for display on the display unit 530. Display unit 530 may be digital and/or analog.

The computer system 500 may also include a main memory 508, preferably random access memory (RAM), and may also include a secondary memory 510. The secondary memory 510 may include, for example, a hard disk drive 512 and/or a removable storage drive 514, representing a floppy disk drive, a magnetic tape drive, an optical disk drive, a flash memory, etc. The removable storage drive 514 reads from and/or writes to a removable storage unit 518 in a well known manner. Removable storage unit 518, represents a floppy disk, magnetic tape, optical disk, etc. which is read by and written to by removable storage drive 514. As will be appreciated, the removable storage unit 518 includes a computer usable storage medium having stored therein computer software and/or data.

In alternative embodiments, secondary memory 510 may include other means for allowing computer programs or other instructions to be loaded into computer system 500. Such means may include, for example, a removable storage unit 522 and an interface 520. Examples of such removable storage units/interfaces include a program cartridge and cartridge interface (such as that found in video game devices), a removable memory chip (such as a ROM, PROM, EPROM or EEPROM) and associated socket, and other removable storage units 522 and interfaces 520 which allow software and data to be transferred from the removable storage unit 522 to computer system 500.

The computer system 500 may also include a communications interface 524. Communications interface 124 allows software and data to be transferred between computer system 500 and external devices. Examples of communications interface 524 may include a modem, a network interface (such as an Ethernet card), a communications port (e.g., serial or parallel, etc.), a PCMCIA slot and card, a modem, etc. Software and data transferred via communications interface 524 are in the form of signals 528 which may be electronic, electromagnetic, optical or other signals capable of being received by communications interface 524. Signals 528 are provided to communications interface 524 via a communications path (i.e., channel) 526. Channel 526 (or any other communication means or channel disclosed herein) carries signals 528 and may be implemented using wire or cable, fiber optics, blue tooth, a phone line, a cellular phone link, an RF link, an infrared link, wireless link or connection and other communications channels.

In this document, the terms "computer program medium" and "computer usable medium" are used to generally refer to media or medium such as various software, firmware, disks, drives, removable storage drive 514, a hard disk installed in hard disk drive 512, and signals 528. These computer program products ("computer program medium" and "computer usable medium") are means for providing software to computer system 500. The computer program product may comprise a computer useable medium having computer program logic thereon. The invention includes such computer program products. The "computer program product" and "computer useable medium" may be any computer readable medium having computer logic thereon.

Computer programs (also called computer control logic or computer program logic) are may be stored in main memory 508 and/or secondary memory 510. Computer programs may also be received via communications interface 524. Such computer programs, when executed, enable computer system 500 to perform the features of the present invention as discussed herein. In particular, the computer programs, when executed, enable processor 504 to perform the functions of the present invention. Accordingly, such computer programs represent controllers of computer system 500.

In an embodiment where the invention is implemented using software, the software may be stored in a computer program product and loaded into computer system 500 using removable storage drive 514, hard drive 512, or communications interface 524. The control logic (software or computer program logic), when executed by the processor 504, causes the processor 504 to perform the functions of the invention as described herein.

In another embodiment, the invention is implemented primarily in hardware using, for example, hardware components such as application specific integrated circuits (ASICs). Implementation of the hardware state machine to perform the functions described herein will be apparent to persons skilled in the relevant art(s).

In yet another embodiment, the invention is implemented using a combination of both hardware and software.

In an example software embodiment of the invention, the methods described above may be implemented in SPSS control language or C++ programming language, but could be implemented in other various programs, computer simulation and computer-aided design, computer simulation environment, MATLAB, or any other software platform or program, windows interface or operating system (or other operating system) or other programs known or available to those skilled in the art.

The invention claimed is:

1. A method for remote monitoring of a patient for sepsis risk indicators comprising:
provisioning the patient with a wearable biometric sensor capable of detecting variables including heart rate, respiratory rate, and activity or acceleration;
detecting the variables of the patient by the biometric sensor;
generating a wireless signal comprising the detected variables by the biometric sensor;
communicating the wireless signal from the biometric sensor to a mobile phone or a mobile application;
measuring variables including temperature and blood pressure of the patient;
inputting the measured variables into the mobile phone or the mobile application;
communicating a mobile signal comprising the detected variables and measured variables from the mobile phone or mobile application to a server;
receiving the mobile signal at a remote location;
determining a risk of sepsis in said patient using the detected variables and measured variables; and
accounting for patient activity in the determination of the risk of sepsis to reduce a rate of a false positive indication of sepsis by (a) excluding from consideration in the determination one or more values of the detected variables that exceed respective predetermined thresholds therefor during the patient activity, and (b) delaying the measuring of the measured variables for a predetermined period of time subsequent to detection of the patient activity including the one or more values.

2. The method according to claim 1, further comprising distinguishing between physical activity-related elevation of vital signs and sepsis-related elevation of the vital signs.

3. The method according to claim 2, further comprising accounting for the physical activity-related elevation of vital signs in determining the risk of sepsis.

4. The method according to claim 3, further comprising diagnosing and treating the patient to reduce the patient's risk of developing sepsis.

5. The method according to claim 1, wherein the server receives the mobile signal.

6. The method according to claim 5, wherein the server is a cloud server.

7. The method according to claim 5, wherein the server determines the risk of sepsis in said patient.

8. The method according to claim 7, wherein the server uses data from the biometric sensor to mask out time periods where heart rate, respiratory rate, temperature, and blood pressure data are likely to have been affected by intense physical activity to preclude a false positive indication of sepsis.

9. The method according to claim 7, wherein the server calculates the patient's risk of sepsis using an algorithm.

10. The method according to claim 9, wherein the algorithm is configured to take into account current clinically-accepted techniques used to assess sepsis.

11. The method according to claim 10, wherein the calculation is according to the following algorithm:
I. Heart Rate:
If average heart rate is $<\frac{1}{2}$ (220-age) bpm, then flag is 0,
If average heart rate is $>\frac{1}{2}$ (220-age) bpm AND
Activity is 1, then flag is 0,
Activity is 0, then flag is 1,
wherein average heart rate is average heart rate over the last 15 minutes with no flag thrown in first 15 minutes,
II. Respiratory Rate:
If average respiratory rate is between 8-22 bpm, then flag is 0,
If average respiratory rate is <8 bpm, then flag is 1,
If average respiratory rate is >22 bpm AND
Activity is 1, then flag is 0
Activity is 0, then flag is 1;

wherein average respiratory rate is average breathing rate over the last 15 minutes with no flag thrown in first 15 minutes, III. Temperature and Blood Pressure:
  If temperature is between 96.8 F-100.4 F, then flag is 0,
  If temperature is below 96.8 F or greater than 100.4 F, then flag is 1,
    wherein, if activity is within last 30 minutes, delay a prompt to measure temperature and blood pressure by 30 minutes, IV. Suspected Infection:
  If 1+major symptom is checked in checklist, then flag is 1,
  If 2+minor symptoms are checked in checklist, then flag is 1,
    wherein, checklist includes fever, diarrhea, and vomiting, and V. Activity:
  If accelerometer values peak 2 standard deviations (Stdev) from average noise level or heart rate (HR) is >50% of maximum AND
    Vitals peak 10-60 seconds or more than 5 minutes, then flag is 0,
    Vitals above 50% of maximum from 1-5 minutes, then flag is 1,
  If accelerometer values <2 Stdev from average noise level or HR is ≤50% of maximum, then flag is 0.

12. The method according to claim 10, wherein the patient is prompted to confirm activity, if accelerometer values peak 2 standard deviations (Stdev) from average noise level or heart rate (HR) is >50% of maximum.

13. The method according to claim 1, wherein the detected variables are continuously monitored and patient activity is tracked in a manner to detect early warning signs of sepsis and allow for more timely interventions to reduce unnecessary readmissions and improve mortality rates.

14. The method according to claim 1, wherein the measured variables are measured at least once per day.

15. The method according to claim 13, wherein the measured variables are measured at least once per day.

* * * * *